United States Patent [19]

Walsh et al.

[11] 4,292,036
[45] Sep. 29, 1981

[54] PROCESS FOR IMPARTING FLAME RETARDANCE TO TEXTILE MATERIALS

[75] Inventors: Edward N. Walsh, New City, N.Y.; Thomas A. Hardy, Fairfield, Conn.

[73] Assignee: Stauffer Chemical Company, Westport, Conn.

[21] Appl. No.: 146,582

[22] Filed: May 5, 1980

[51] Int. Cl.³ .............................. C07F 9/11; C07F 9/40; D06M 1/00; D06M 13/34
[52] U.S. Cl. ...................................... 8/182; 8/184; 8/185; 8/187; 8/116 P; 252/608; 260/943; 427/393.3; 525/2
[58] Field of Search .................. 8/115.6, 115.7, 116 P, 8/184, 185, 186, 187, 182; 427/393.3; 260/45.9 NP, 943; 528/254, 259, 266; 525/2; 252/8.1

[56] References Cited

U.S. PATENT DOCUMENTS 4,177,300 12/1979 Walsh et al. .................... 427/393.3

Primary Examiner—Michael R. Lusignan
Attorney, Agent, or Firm—William C. Gerstenzang

[57] ABSTRACT

Flame retardance is imparted to textile materials by impregnating them with a flame retardant composition comprising
(a) at least one compound represented by the formula

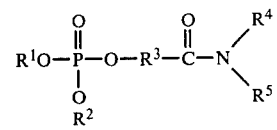

wherein $R^1$ and $R^2$ are each independently selected from the group consisting of aryl, arylalkyl, alkylaryl, alkenyl and alkyl having from 1 to about 6 carbon atoms and

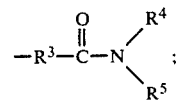

$R^3$ represents an alkylene group having from 1 to about 5 carbon atoms, and $R^4$ and $R^5$ are each independently selected from the group consisting of hydrogen,

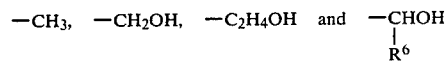

wherein $R^6$ represents an alkyl group having from 1 to about 4 carbon atoms; provided that not all of said $R^4$'s and $R^5$'s are —$CH_3$ at the same time:
(b) an aminoplast; and
(c) an acid catalyst; and heating the impregnated textile material sufficiently to cure said flame retardant composition.

7 Claims, No Drawings

PROCESS FOR IMPARTING FLAME RETARDANCE TO TEXTILE MATERIALS

BACKGROUND OF THE INVENTION

The present invention relates to a process for imparting flame retardance to textile materials. More particularly, the present invention relates to a process for imparting flame retardance to textile materials which comprises impregnating the textile materials with a flame retardant composition comprising a phosphoroxycarboxamide compound, and curing the so impregnated flame retardant composition.

It has long been known that flame retardant properties may be incorporated into textile materials such as cotton fabric or yarn by treatment with phosphorus-containing compounds. Such compounds are usually in the form of organophosphorus compounds which are relatively harmless to the material being treated as well as resistant to laundering.

More recently, it has been discovered that organic nitrogen is a synergist for phosphorus-induced flame retardance in cellulosic fabrics, and its presence in the flame-retardant compound permits a reduction in the amount of flame retardant which is required to achieve an acceptable degree of flame retardance. Exemplary of flame-retardant compounds which contain both nitrogen and phosphorus are those disclosed in U.S. Pat. Nos. 3,268,292; 3,374,292; 3,556,840; 3,634,422; 3,763,283; 3,835,204 and 4,162,279.

It is an object of the present invention to provide a novel process for imparting flame retardance to textile materials.

In accordance with the present invention, there is provided a process for imparting flame retardance to textile materials comprising the steps of impregnating the textile material with a flame-retardant composition comprising:

(a) at least one phosphoroxycarboxamide represented by the formula:

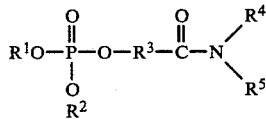

wherein $R^1$ and $R^2$ are each independently selected from the group consisting of aryl, arylalkyl, alkylaryl, alkenyl and alkyl having 1 to 6 carbon atoms and

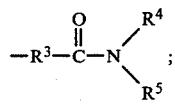

$R^3$ represents an alkylene group having from 1 to about 5 carbon atoms, and $R^4$ and $R^5$ are each independently selected from the group consisting of hydrogen,

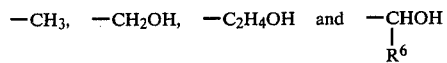

wherein $R^6$ represents an alkyl group having from 1 to about 4 carbon atoms; provided that not all of the $R^4$'s and $R^5$'s are —$CH_3$ at the same time;

(b) an aminoplast; and
(c) an acid catalyst and heating the impregnated textile material to a temperature sufficient to cure the flame-retardant composition.

The phosphoroxycarboxamides may be prepared by a variety of techniques known in the art. They may, for example, be prepared by reacting a carboalkoxy phosphate with ammonia to form an N-unsubstituted phosphoroxycarboxamide, as follows:

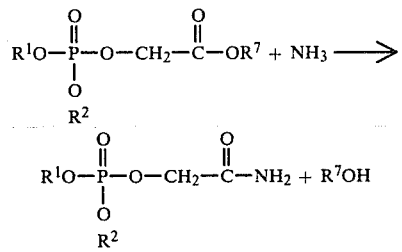

wherein $R^1$ and $R^2$ are as hereinbefore defined, and $R^7$ represents an alkyl group having from 1 to 2 carbon atoms.

Partially N-substituted phosphoroxycarboxamides may be prepared by substituting a primary amine, such as methyl amine or ethanolamine for the ammonia in the illustrated scheme for preparing N-unsubstituted phosphoroxycarboxamides. Also, secondary amines can react and be used similarly; however, there must be at least one primary amino or ammonia type amide present to provide a reactive site.

This reaction may be conducted in a solvent which is nonreactive towards either the starting reagents or the resulting phosphoroxycarboxamide. Suitable solvents include, but are not limited to methanol, ethanol, ethylene glycol, diethyl ether, acetone, toluene, and the like. The reaction is conducted at a temperature ranging from about 0° C. to about 40° C. and generally requires a reaction time ranging from about 2 to about 20 hours.

The carboalkoxy phosphate precursors used in preparing the phosphoroxycarboxamides may be prepared by reacting an alkyl phosphate with an alkyl haloalkanoate at a temperature ranging from about 125° C. to about 175° C. in the presence of an anionic catalyst such as sodium carbonate at a concentration ranging from about 0.2 percent to about 0.5 percent by weight of total reaction mixture. This reaction is generally conducted without a solvent and requires from about 8 to about 12 hours at the stated temperature range. Typical alkyl phosphates which may be used in preparing these precursors include, but are not limited to, trimethyl phosphate, triethyl phosphate, tripropyl phosphate, tributyl phosphate, and the like.

Exemplary of the alkyl haloalkanoates which may be used to form the precursor phosphonate compounds are methyl chloroacetate, ethyl chloroacetate, ethylbromoacetate, and the like.

Thus, the formation of precursors may be illustrated schematically as follows:

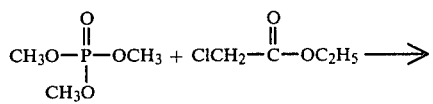

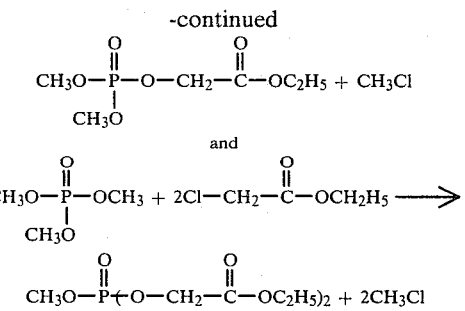

$$CH_3O-\overset{\underset{\|}{O}}{\underset{CH_3O}{P}}-O-CH_2-\overset{O}{\underset{\|}{C}}-OC_2H_5 + CH_3Cl$$

and $$CH_3O-\overset{\underset{\|}{O}}{\underset{CH_3O}{P}}-OCH_3 + 2Cl-CH_2-\overset{O}{\underset{\|}{C}}-OCH_2H_5 \longrightarrow$$

$$CH_3O-\overset{\underset{\|}{O}}{P}(O-CH_2-\overset{O}{\underset{\|}{C}}-OC_2H_5)_2 + 2CH_3Cl$$

The N-unsubstituted or partially substituted phosphoroxycarboxamides, which are prepared by reacting the precursor phosphates with either ammonia or a primary amine, may then be reacted with an aldehyde to form the alkylolamides. Aldehydes which may be used for this purpose include, but are not limited to, formaldehyde, acetaldehyde, and glyoxal. The alkylolamides may then be reacted with an aminoplast to form a water-insoluble resin. Aminoplasts which may be used for this purpose include, but are not limited to, methylol- and methoxymethylmelamines, methylolated ureas, and cyclic ureas such as dimethyloldihydroxyethyleneurea.

For example, the phosphoroxycarboxamides may be methylolated by reaction with formaldehyde, which can be in gaseous, liquid solution, or solid form, over a period of from about 0.5 to about 2 hours at a temperature ranging from about 55° to about 85° C. while maintaining the system at an alkaline pH, preferably in the range of about 7.5 to about 8.5. The product of this reaction will be a mixture of a monomethylol substituted derivative and a dimethylol derivative:

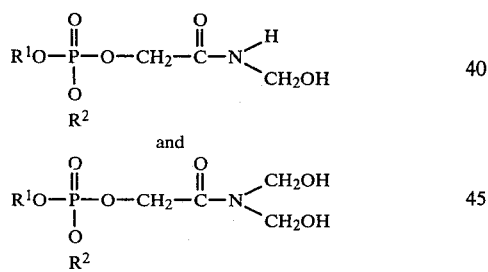

wherein the specific proportions of the mono- and di-methylol derivatives within the mixture depends, in part, upon the molar ratio of the formaldehyde relative to the unsubstituted phosphoroxycarboxamide present in the initial reaction mixture. Although completely satisfactory in this form for most applications, it is understood that, if desired, the reaction product may be further refined by techniques well-known in the art to obtain the desired compound in a more pure form such as, for example, by crystallization.

The partially substituted phosphoroxy-carboxamides may also be reacted with formaldehyde to form N-methylol substituted derivatives, i.e.,

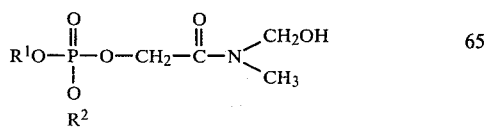

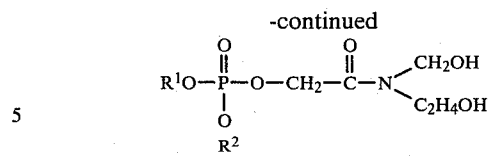

Exemplary phosphoroxycarboxamides which may be used in the practice of this invention are: O,O-dimethyl phosphoroxyacetamide:

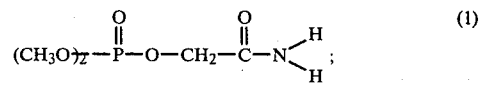

N-methylol O,O-dimethyl phosphoroxyacetamide:

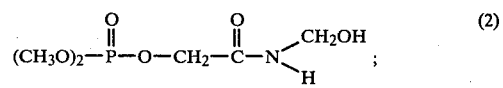

N-methyl-N-methylol, O,O-dimethyl phosphoroxyacetamide:

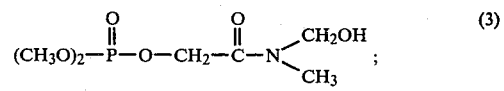

N,N-dimethylol, O,O-dimethyl phosphoroxyacetamide:

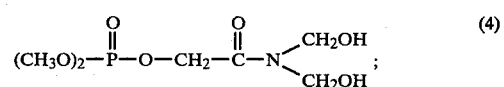

O,O-dipropyl phosphoroxyacetamide:

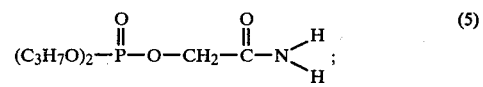

O,O-diallyl phoroxyacetamide

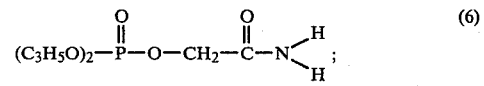

O,O-diethyl phosphoroxypropionamide:

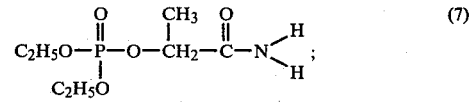

N-methylol, O,O-diethyl phosphoroxyacetamide:

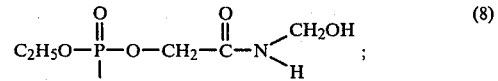

N-methyl, N-hydroxyethyl, O,O-diethyl phosphoroxyacetamide:

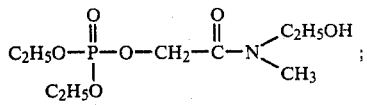
(9)

Methyl bis(carbamidomethyl) phosphate:

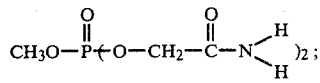
(10)

Ethyl bis(carbamidomethyl) phosphate:

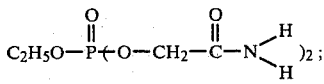
(11)

Bis(dimethylol carbamidomethyl) ethyl phosphate:

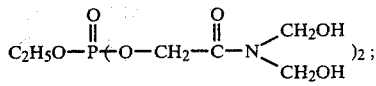
(12)

Methyl bis(N-methyl-N-methylol carbamidomethyl) phosphate:

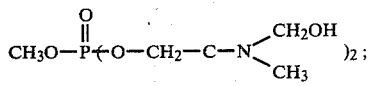
(13)

The unsubstituted phosphoroxycarboxamides and the partially substituted phosphoroxycarboxamides can be bonded to a textile by means of a reaction with an aminoplast. Thus, for example, an unsubstituted phosphoroxycarboxamide such as O,O-dimethyl phosphoroxyacetamide can be admixed with about 0.2 to 5 parts by weight of tri-, tetra-, or pentamethylolated melamine, or a partially etherified derivative thereof, and cured in the presence of an acid catalyst such as those hereinabove described so as to yield durable flame retardant finishes on cellulosic, cellulose-polyester, or other textiles. Methylolation of the phosphoroxycarboxamide does, however, offer the advantage of making it reactive with cellulose as well as with the aminoplast and thus generally minimizes the amount of aminoplast which is required.

The phosphoroxycarboxamides may be applied to normally flammable substrates in the form of an aqueous flame retardant formulation or as a liquid formulation in any of the organic solvents commonly used in the solvent finishing of textiles including, for example, ethanol, methanol, chloroform, water and mixtures thereof. Preferably, these formulations also include an aminoplast and an acid catalyst.

The term "aminoplast" is here meant to denote a nitrogen-containing resin which is capable of reacting with itself, with the phosphoroxycarboxamides of the present invention, and/or with the textile or other substrate and which is prepared by the polycondensation of formaldehyde with a compound having at least two reactive amino or amido hydrogen atoms. Exemplary of the aminoplasts which may be used are methylolureas which may be either straight chain or cyclic, methylolmelamines, methylolcarbamates, methylolurons, methylolamides, and methyl ethers of the abovelisted methylol compounds, methylolated acid amides, urea glyoxal condensation products, urea-glyoxalformaldehyde condensation products, N-methylolated or N,N-dimethylolated O-alkyl, O-alkoxy, or O-hydroxyalkyl carbamates. Preferred aminoplasts include tris (methoxymethyl) melamine as sold by the American Cyanamid Company under the trademark "AEROTEX M-3"; partially methylated melamine as sold by the American Cyanamid Company under the trademark "AEROTEX 23 SPECIAL"; dimethylolethylene urea; dimethylol dihydroxyethylene urea, dimethylol methyl carbamate, dimethylol hydroxyethyl/hydroxypropyl carbamate, and dimethoxymethyl uron. For most purposes, the use of one or more of the above-described aminoplasts at a concentration ranging from 10 to 600 percent and preferably from about 25 to 300 percent by weight of the phosphoroxycarboxamide will be satisfactory.

Suitable acidic catalysts for use in the practice of the present invention include mineral acids such as phosphoric acid; organic acids such as oxalic, citric, succinic, maleic, glycolic, chloroacetic, and toluenesulfonic acids; alkyl acid phosphates, and the like. Also included are the salts of strong acids with relatively weak bases such as, for example, zinc nitrate, zinc chloride, magnesium chloride, ammonium chloride, ammonium phosphates, and amine hydrochlorides. Some typical amine hydrochlorides include 2-amino-2-methylpropanol hydrochloride sold under the tradename "Catalyst AC" by the Monsanto Company, and the alkanolamine hydrochloride sold as "Catalyst XRF" by the Millmaster Onyx Corporation. The use of one or more of these catalysts at a concentration of from about 0.01 to 5 percent based on the weight of the phosphoroxycarboxamide will be suitable for most purposes.

The concentration (i.e., the "solids" content) of the phosphoroxycarboxamide/aminoplast/catalyst composition used may vary in accordance with several factors such as the nature of the substrate or fabric to which it is being applied, the amount of phosphoroxycarboxamide resin desired in or on the final product, and the like. It is generally desirable, however, to achieve a phosphorous uptake on the textile or other substrate ranging from about 1 to about 5 percent by weight of the dry untreated fabric or substrate. Thus, the concentration of the flame-retardant composition will be adjusted to a solids level which will produce the desired amount of phosphorous uptake with the anticipated amount of wetpickup. The ranges given, of course, are merely illustrative and may be varied in accordance with the particular needs of the user.

The flame-retardant composition containing the phosphoroxycarboxamide, aminoplast, and catalyst may be applied to textiles or other substrates by the use of any of those techniques known in the art for this purpose such as dipping, spraying, painting, padding, etc. A preferred method for applying the composition to a fabric is that known as "padding" wherein the fabric is passed or "padded" through the composition while the latter is being held in a tank or other suitable container. For most applications, it is desirable to maintain the pH of the padding bath in the range of from about 4.5 to about 5.5.

The thus-applied flame-retardant composition may then be dried and cured. Drying may be accomplished by various techniques including heating at a temperature ranging from room temperature up to about 120° C. or higher. It is, of course, entirely possible to eliminate drying as a separate step and accomplish the drying as a part of the curing step. Curing may be accomplished by heating at a temperature ranging from about 130° C. to about 180° C. with temperatures in the range of from about 150° C. to 160° C. being preferred. Curing time may vary from about 1 minute to about 20 minutes depending on the nature of the substrate being treated. The effect of the curing operation is to cause the phosphoroxycarboxamide and aminoplast to react with the cellulose or with each other so as to form a crosslinked, insoluble finish in and/or on the individual fibers comprising the textile or other flammable substrate.

As used herein, the term "flame retardant" is intended to refer to that particular property of a material which provides it with a degree of resistance to ignition and burning. Thus, a fire or flame retardant textile, paper, or other solid substrate is one which has a low level of flammability and flame spread. This property may be conveniently evaluated by means of any of the standard flame retardancy tests described in the Federal Flammability Standard of July 27, 1971 (35 Federal Register 146).

As used herein, the term "textile" or "textiles" is meant to encompass woven or knitted fabrics as well as non-woven fabrics which consist of continuous or discontinuous fibers bonded so as to form a fabric by mechanical entanglement, thermal interfiber bonding, or by use of adhesive or bonding substances. Such non-woven fabrics may contain a certain percentage, up to 100 percent, of wood pulp as well as conventional textile fibers in which case part of the bonding process is achieved by means or hydrogen bonding between the cellulosic pulp fibers.

I claim:

1. A process for imparting flame retardance to a textile material comprising the steps of
   (a) impregnating said textile material with a flame-retardant composition comprising
      (1) at least one compound represented by the formula

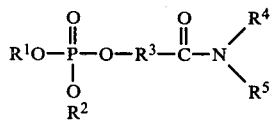

wherein $R^1$ and $R^2$ are each independently selected from the group consisting of aryl, arylalkyl, alkylaryl, alkenyl and alkyl having from 1 to about 6 carbon atoms and

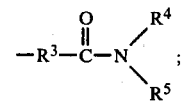

$R^3$ represents an alkylene group having from 1 to about 5 carbon atoms, and $R^4$ and $R^5$ are each independently selected from the group consisting of hydrogen,

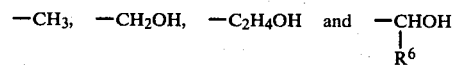

wherein $R^6$ represents an alkyl group having from 1 to about 5 carbon atoms, provided that not all of said $R^4$'s and $R^5$'s are —$CH_3$ at the same time;
   (b) an aminoplast; and
   (c) an acid catalyst; and
      (2) heating said impregnated textile material sufficiently to cure said flame-retardant composition.

2. The process of claim 1 wherein $R^1$ and $R^2$ are each independently selected from the group consisting of alkyl radicals having from 1 to 2 carbon atoms, $R^4$ and $R^5$ are each independently selected from the group consisting of hydrogen, —$CH_3$, —$CH_2OH$ and —$C_2H_4OH$ and $R^3$ represents —$CH_2$—.

3. The process of claim 2 wherein said compound is O,O-dimethyl-phosphoroxyacetamide.

4. The process of claim 2 wherein said compound is N-methylol O,O-dimethylphosphoroxyacetamide.

5. The process of claim 1 wherein said aminoplast is selected from the group consisting of straight chained or cyclic, methylolmelamines, methylolcarbamates, methylolurons, methylolamides, the methyl ethers of the above listed methylol compounds, methylolated acid amines, urea glyoxal condensation products, urea-glyoxalformaldehyde condensation product, N-methylolated or N,N-dimethylolated O-alkyl, O-alkoxy, or O-hydroxyalkyl carbamates or mixtures thereof.

6. The process of claim 5 wherein said acid catalyst is selected from the group consisting of phosphoric acid, oxalic acid, citric acid, succinic acid, maleic acid, glycolic acid, chloroacetic acid, toluenesulfonic acid, zinc nitrate, zinc chloride, magnesium chloride, ammonium chloride, ammonium phosphates and amine hydrochlorides.

7. The process of claim 6 wherein said heating takes place at a temperature ranging from about 130° C. to about 180° C.

* * * * *